United States Patent [19]

Young

[11] 4,286,880
[45] Sep. 1, 1981

[54] SCANNING LIGHT BEAM LUMBER DEFECT POSITION SYSTEM AND METHOD OF USING SAME

[75] Inventor: Allen E. Young, Highland, Mich.

[73] Assignee: The Bendix Corporation, Southfield, Mich.

[21] Appl. No.: 61,977

[22] Filed: Jul. 30, 1979

[51] Int. Cl.³ .................. G01N 21/89; G06M 7/00
[52] U.S. Cl. .................... 356/431; 250/221; 350/6.91; 356/375; 356/383
[58] Field of Search ............ 356/430, 431, 237, 375, 356/383; 250/221; 350/6.91, 6.8

[56] References Cited

U.S. PATENT DOCUMENTS

| | | | |
|---|---|---|---|
| 3,360,654 | 12/1967 | Müller | 250/221 X |
| 3,851,168 | 11/1974 | Erbstein | 250/221 |
| 3,858,043 | 12/1974 | Sick et al. | 250/221 |
| 3,898,469 | 8/1975 | Nichols et al. | 250/563 |
| 3,925,049 | 12/1975 | Schwenninger | 65/29 |
| 3,942,021 | 3/1976 | Barr et al. | 250/572 |
| 3,976,384 | 8/1976 | Matthews et al. | 356/237 X |
| 4,025,198 | 5/1977 | Hutchins | 356/237 X |
| 4,118,127 | 10/1978 | Klein et al. | 356/431 |
| 4,144,449 | 3/1979 | Funk et al. | 250/221 |
| 4,149,089 | 4/1979 | Idelsohn et al. | 250/563 |

*Primary Examiner*—Vincent P. McGraw
*Attorney, Agent, or Firm*—Markell Seitzman; Russel C. Wells

[57] ABSTRACT

In a lumber inspection and optimization system, an electro-optical defect position scanner is combined with a voice recognition device to enable a human inspector to locate and classify flaws on the surface of a board. The human inspector, by means of an indicator, pierces a light curtain to electro-optically locate a flaw. The indicator can be used to enhance the flaw by physically marking the board. With voice recognition, the human inspector can vocally classify the flaw. These voice classifications are later correlated with flaw information and used to process the board into its finished products.

22 Claims, 13 Drawing Figures

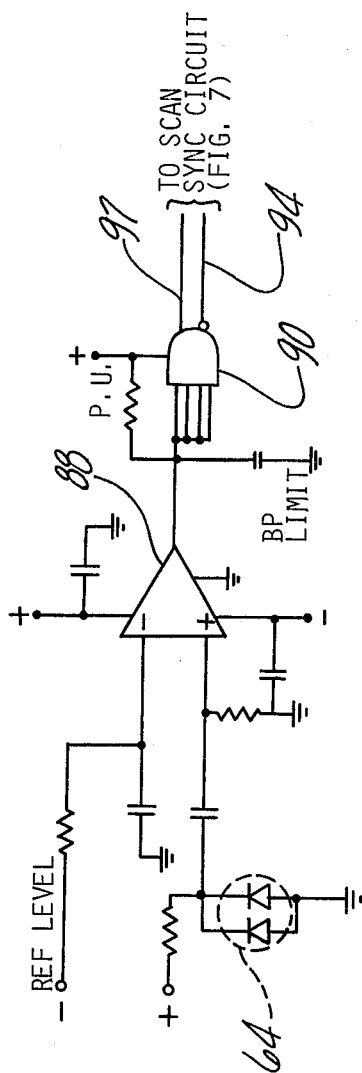
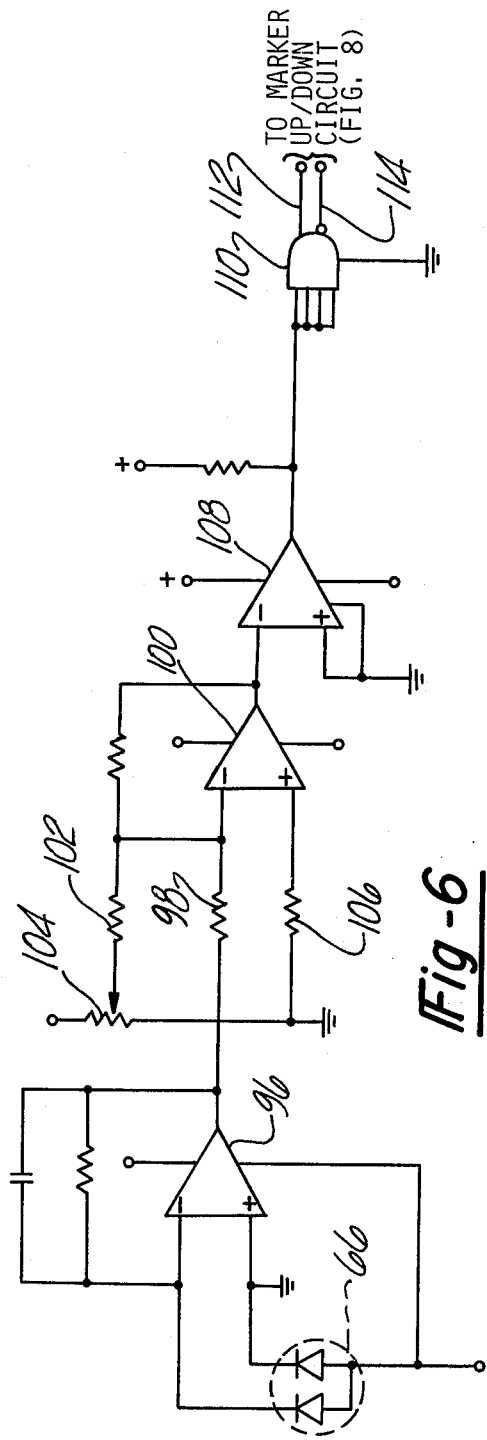
Fig-5
Fig-6

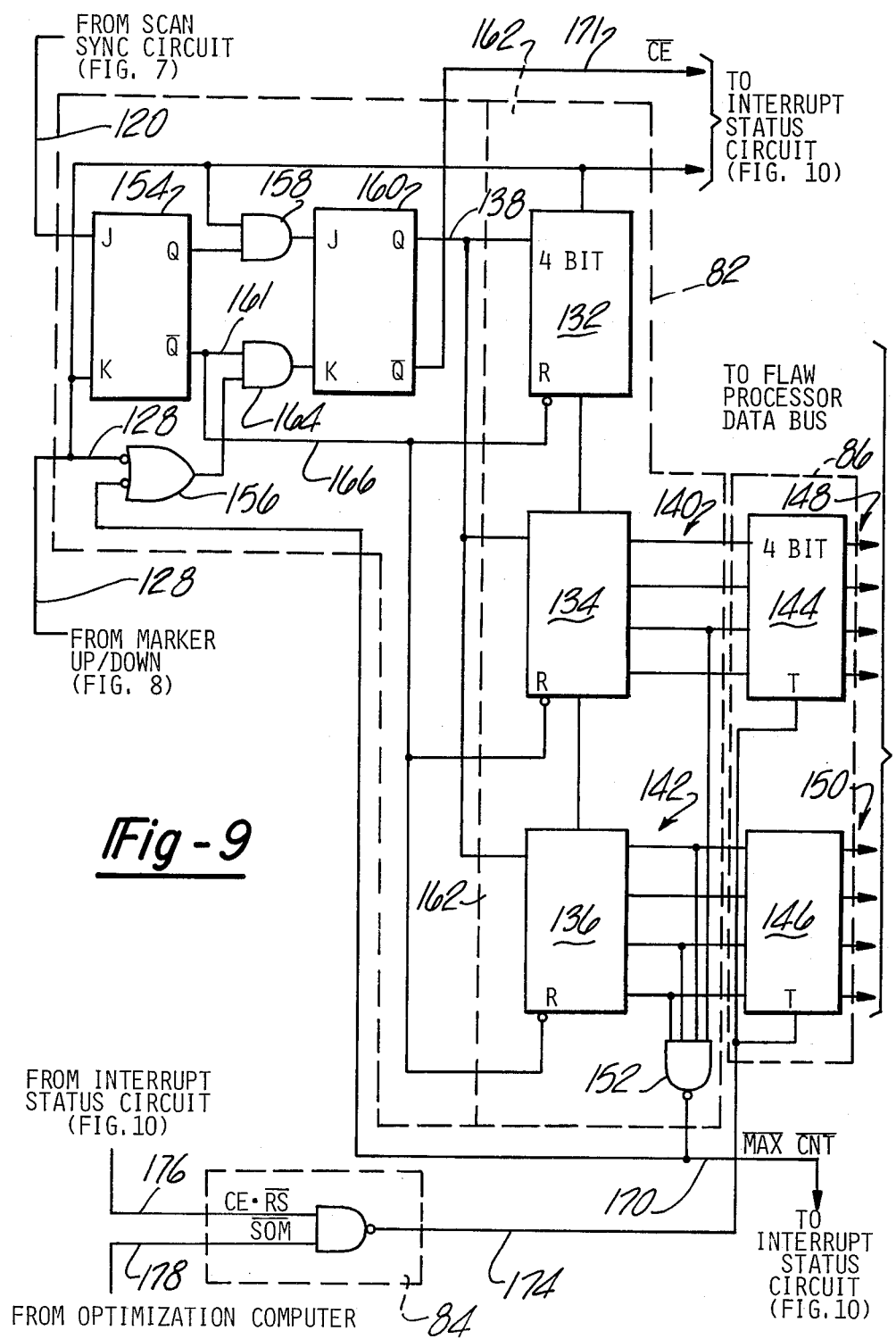

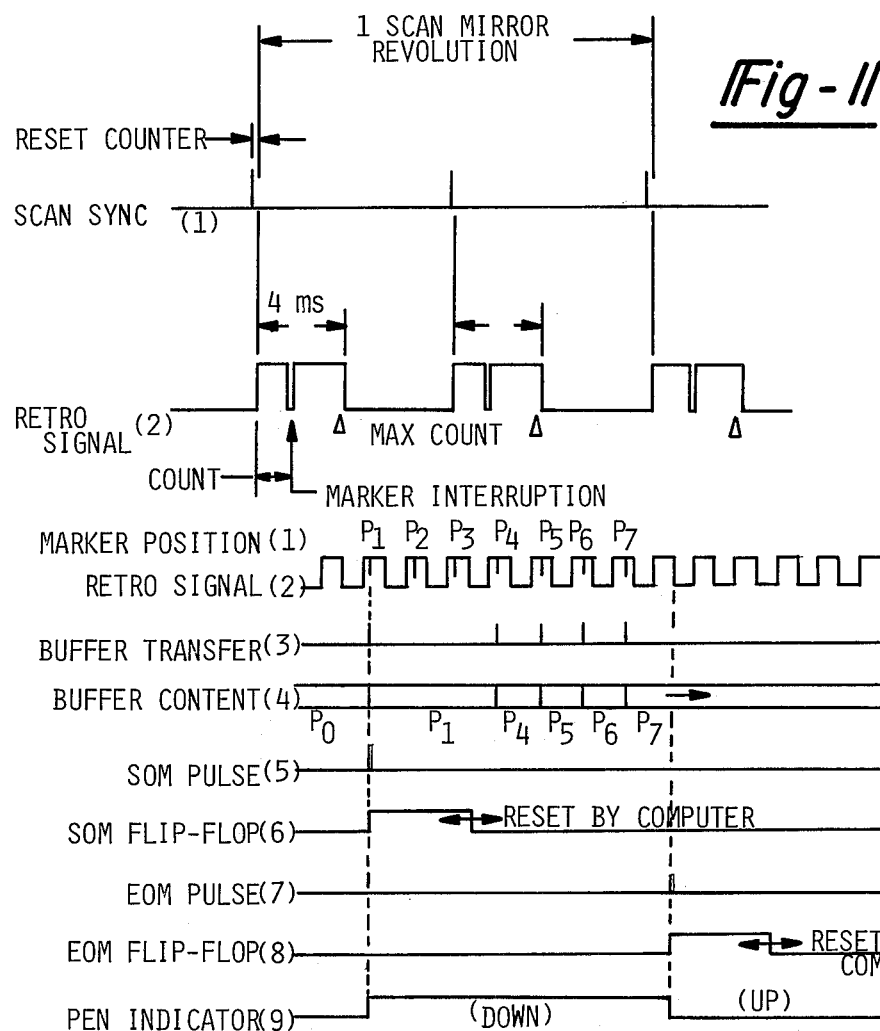
Fig-11
Fig-12
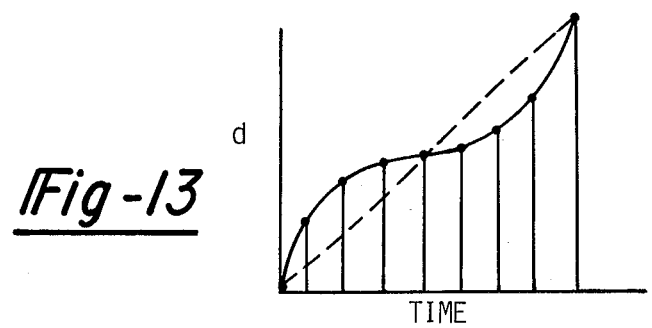
Fig-13

SCANNING LIGHT BEAM LUMBER DEFECT POSITION SYSTEM AND METHOD OF USING SAME

BACKGROUND OF THE INVENTION

1. Field of the Invention

The present invention relates to systems maximizing the utilization of materials having irregular and unpredictable flaws and defects such as found in forest products, plate glass, sheet metal and the like. More particularly, the invention relates to a defect position scanner generating flaw data indicative of the location and size of the flaws and having a human operated classification device generating data indicative of the flaw class.

2. Prior Art

The woodworking industries are faced with maximizing the utilization of available lumber in the face of a wide range of required end products. Each facility must analyze an incoming board to determine how it may be cut to most efficiently meet the requirements of the particular production order. Often, an experienced human inspector evaluates each board and makes an on-the-spot determination regarding the most efficient way to cut a particular board. It is recognized that such human inspection is inefficient, and subject to periodic vagaries caused by operator distractions and fatigue.

Accordingly, a variety of systems to aid or replace the human inspector have been proposed. One such system is disclosed by Idelsohn et al, in U.S. Pat. No. 4,149,089 entitled "Electro-Optical Scanner for Generating Digital Data" which issued on Apr. 10, 1979; another system is disclosed by Freedman et al, in U.S. Patent Application Ser. No. 8,891 (a continuation-in-part of U.S. Ser. No. 818,252), filed on Feb. 2, 1979, and entitled "Lumber Inspection and Optimization System", all of which are expressly incorporated by reference. These systems combine the speed of electro-optical scanning for flaw detection and location with a computer for optimizing the manner in which a board is to be cut. These systems include an upstream human inspector station (UHI), an electro-optical scanner, a flaw processor, a lumber optimization computer, an order entry device and an output station. At the inspector station, a human inspector may inhance a flaw ("flaw" and "defect" are used interchangeably herein) for positive detection by the electro-optical line scanner or may suppress unobjectionable characteristics (such as dirt or footprints, etc.) which the electro-optical line scanner would detect as an objectionable flaw. The electro-optical line scanner, as taught by Idelsohn, scans opposite sides of the board in a sequentially interlaced scanning pattern in a direction normal to the direction of movement of the board to generate scan data indicative of the surface characteristics and the location of the flaws on both sides of the board.

The flaw processor receives data from the electro-optical line scanner and generates enlarged rectangles about each detected flaw to compensate for defective lumber usually surrounding each flaw and then stores the location of the coordinates of the enlarged rectangles in a flaw data buffer. If the order being processed includes pieces of lumber which may have predetermined classes of defects, the inspector station further includes a defect classification device operated by the human inspector which generates data indicative of the class of each flaw. This flaw class is subsequently combined with the scan data in the flaw processor and stored in the flaw data buffer.

The lumber optimization computer compares the data in the flaw data buffer with the desired product data received from the order entry device and computes, in accordance with a predetermined program, the optimum way in which the board is to be cut. The order entry device enters into the computer the size, priority and classes of permitted flaws for each different piece desired for the order being processed for a particular run, day and/or facility. The output station receives the data from the lumber optimization computer and either marks the lumber at the location where it is to be cut, or actuates a saw to cut the lumber, as determined by the lumber optimization computer.

The foregoing system overcomes many of the prior art deficiencies by combining the judgment capabilities of a human inspector with the speed of an electro-optical line scanner in a manner to provide real time information to the computer in useable form and in an efficient manner.

While the use of the electro-optical line scanners provides an adequate indication of the sizes and location of the flaws, it cannot discriminate between acceptable (e.g., certain knots for particular desired end products) and unacceptable flaws. Often, it is necessary to suppress acceptable defects or certain surface characteristics with a special ink (or enhance certain other unacceptable defects with another type of ink to insure detection by the electro-optical line scanner). This additional step is awkward and time consuming often requiring running the board through the system at a slower than optimal speed. It may be necessary to slow down the speed of the board passing through the inspection station as disclosed by Idelsohn et since it is necessary to enter defect class information via a keyboard as the defect reaches a narrow work area such as a predetermined point, or line in the inspector station.

Accordingly, the invention comtemplates an improvement to the above described limber inspection and optimization systems by application of light scanning techniques specifically, the use of a high speed laser beam to generate a light curtain or barrier.

This implementation uses a beam splitter as opposed to the apertured mirror of the present invention. The significance of the beam splitter is that the intensity of the light received by the photodetector may be reduced to 25% of intensity of the light source. The light received by the photodetector of the present invention is of virtually the same intensity as that of the light emanations from the light source.

The invention comprises an upstream visual inspection station, an electro-optical line scanner for detecting the sizes and locations of flaw in lumber and for generating data indicative of these flaws and a computer for processing the flaw data to determine the optimum way the board is to be cut. The inspection station includes a defect position scanner which employs a laser beam that is projected by a rotating mirror into a parabolic reflector strip to provide a parallel-ray beam or light curtain of predetermined length. The light curtain is positioned just above the surface of the moving board. An interruption of this beam will occur when the inspector places a marking pen or indicator on to the moving board to indicate the beginning and the end point of an objectionable defect. The interrupted signal is processed to generate digital signals representative of the position of the defect along the board. Mirrors positioned adjacent the defect position scanner permit the inspector to simultaneously view opposite sides of the board and to indicate the positions of flaws on either side. A voice recognition device is provided which permits the inspector to designate classes of defects as he is positioning the indicator. The digital signals from the defect position scanner are combined with the signals from the voice recognition device and with scan data from the electro-optical line scanner into a format useable by the computer. The defect position scanner stores defect position information and transmits an interrupt signal to the computer each time the position of the beginning or of the end of a defect is stored in the defect position scanner. This advantageously permits the stored position information to be removed from storage under the control of the computer while the presence or absence of an indicator is being continuously monitored by the defect position scanner.

Another advantage of the present system is that flaw location and voice classification enhancement or suppresion of the flaws can be performed simultaneously by the operator.

Another advantage of the system is the increased sensitivity achieved by replacing the beam splitter as used in prior scanning devices with an apertured mirror. The apertured mirror eliminates virtually all of the optical signal attentuation associated with a beam splitter.

A further advantage of the invention is the enlarged working area provided for defect locating.

A further advantage of the invention is that flaws can be indicated using a non-cooperative marker or indicator.

The object of the present invention is to provide accurate defect position and class information to a computerized lumber inspection and optimization system without sacrificing the speed at which it is desirable to inspect and process the lumber.

Other objects, features and advantages of the invention will become apparent from the following description thereof, taken together with the accompanying drawings and claims.

BRIEF DESCRIPTION OF THE DRAWINGS

FIG. 5 is an electrical schematic wiring diagram of the start scan photodetector circuit of FIG. 3.

FIG. 6 is an electrical schematic wiring diagram of the retro-reflected signal (RS) photodetector circuit of FIG. 3.

FIG. 9 is an electrical schematic wiring diagram of the position counter, transfer and position buffer circuits of FIG. 4.

FIG. 11 is a timing diagram illustrating one cycle of mirror rotation.

FIG. 12 is a timing diagram further illustrating the operation of the present invention.

FIG. 13 showing the variations in the scan distance (d) as a function of time.

BRIEF DESCRIPTION OF THE PREFERRED EMBODIMENT

Figure 1:
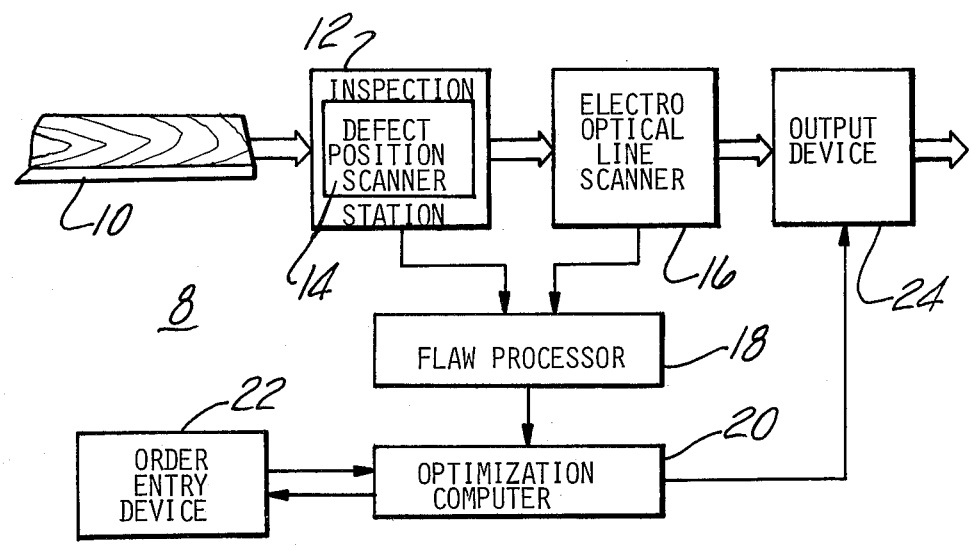
FIG. 1 is a block diagram illustrating the basic elements of a lumber inspection and optimization system which utilizes a defect position scanner.
Figure 2:
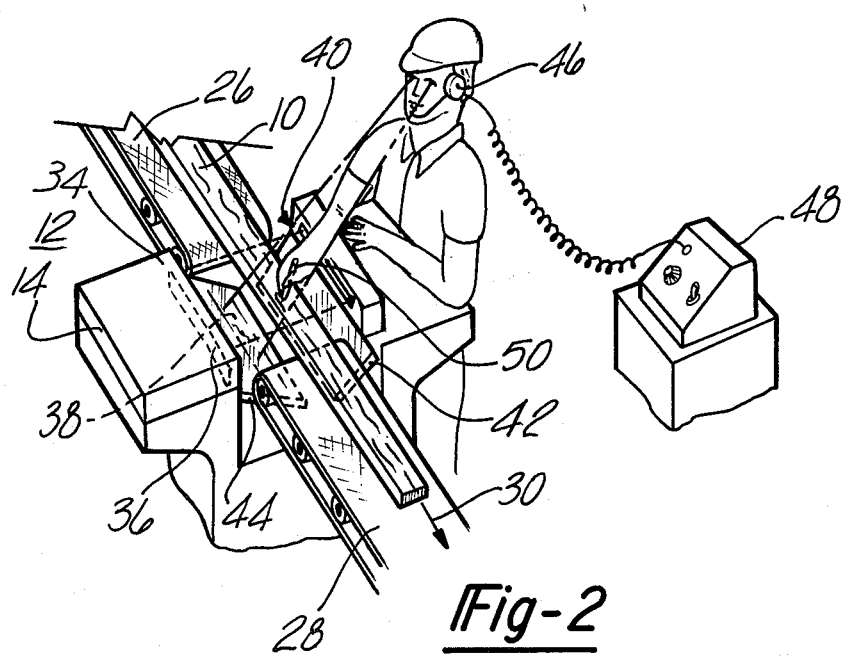
FIG. 2 is a partial perspective view of the defect position scanner with a piece of lumber supported between two conveyor belts and disposed below the light curtain generated by the defect position scanner.

Referring now to FIGS. 1 and 2, there is shown a block diagram of a lumber inspection and optimization system, generally designated 8. The broad arrows show the path of an incoming piece of lumber, illustrated as a board 10, through the inspection and optimization system 8, while the narrow lines show the data flow through the system. The lumber inspection and optimization system 8 comprises an inspection station 12, which includes a defect position scanner 14, an electro-optical line scanner 16, a flaw processor 18, a lumber optimization computer 20, an order entry device 22 responsive to inputs from a human inspector and an output device 24. The board is carried on a conveyor system (FIG. 2) past the defect position scanner 14 located in the inspection station 12, where it is inspected by a human inspector who points to defects or flaws with an indicator 50. The inspector may also enhance certain flaws in the board which may be difficult to detect optically by marking the board with a suitable marking pen. Advantageously, the marking pen may also be utilized as the indicator 50. The defect position scanner 14 under inspector control detects and stores the position of the defects (in the form of digital signals) for controlled transfer to the flaw processor 18. The inspection station 12 may also include a defect classification input control device 48 which permits the human inspector to audibly classify certain types of flaws using microphone 46. The latter information is transformed into electrical data and stored in the flaw processor 18 for later combination with the data generated by the defect position scanner 14. The defect classification input control 48 may be a voice recognition device such as manufactured by the Threshold Technology, Inc. of Delram, N.J.

After passing through the defect position scanner 14, the board 10 passes through the electro-optical line scanner 16 which electro-optically scans both sides of the board and generates scan data indicative of board size and the size, shape and location of the defects contained thereon. The defect position and defect class data from the inspection station 12 and the scan data from the line scanner 16 are processed in the flaw processor 18 to generate flaw data which is processed by the optimization computer 20. Techniques for combining data are well known and will not be elaborated upon.

Physical descriptions of the desired products required for production are entered into the order entry device 22, which may be a tape or card reader, a keyboard or any other device capable of entering the description of the desired products into the computer.

Data from the order entry device 22 and data from the flaw processor 18 are input into the lumber optimization computer 20 where the utilization of the lumber in the board is maximized in accordance with the flaw data and the order entry data (i.e., desired products). The optimization computer 20, may be of the type as disclosed by Idelsohn, et al which computes the cutmarks determining where the board 10 is to be cut and outputs this information into the output device 22, which in turn, either marks or cuts the board 10.

Portions of an inspector station 12 are shown in FIG. 2 and include a pair of spaced in-line conveyor belts 26 and 28, which are arranged to support and propel the board 10 at a predetermined speed past the defect position scanner 14. The defect position scanner 14 includes a housing 34 (approximate dimensions 18×42×6 inches) having a rectangular window 36 (30 to 36 inches wide) provided in one of the sides thereof, adjacent to the conveyor belts 26 and 28. As will be explained in greater detail below, light beams (the individual beams being generally perpendicular to the direction of movement of the board 10) form a light curtain 38 projected through the window 36 slightly above the top surface of the board 10 onto a surface of a reflective strip, i.e., retro-reflector 40. The inspection station 12 further includes a pair of mirrors 42 and 44 suitably disposed below and adjacent to the board 12, and arranged to project an image of the bottom surface of the board 10 on to mirror 44 permitting the inspector view of both sides of the board.

In operation, as the board 10 passes through the inspection station 12 the inspector points to defects by inserting the indicator 50 or marking pen, into the light curtain 38 at the leading edge of the defect while the defect is anywhere within the light curtain 38 (i.e., work area) and removes the marking pen or indicator 50 from the light curtain 38 at the trailing edge of the defect. The indicator 50 may be inserted into and removed from defect-position scanner 14 while the defect is at any position under the light curtain 38 therein providing the inspector with a working area equal to the width of the light curtain 38. The inspector may enhance defects with the indicator and/or verbally transmits defect class designations into the microphone 46. As will be explained in greater detail below, digital defect position information is transmitted from the defect position scanner 14 to the flaw processor 18 where it is combined with the outputs from the voice recognition device 48 and defects from the electro-optical line scanner 16 (FIG. 1) to generate flaw data for use by the optimization computer 20.

Figure 3:
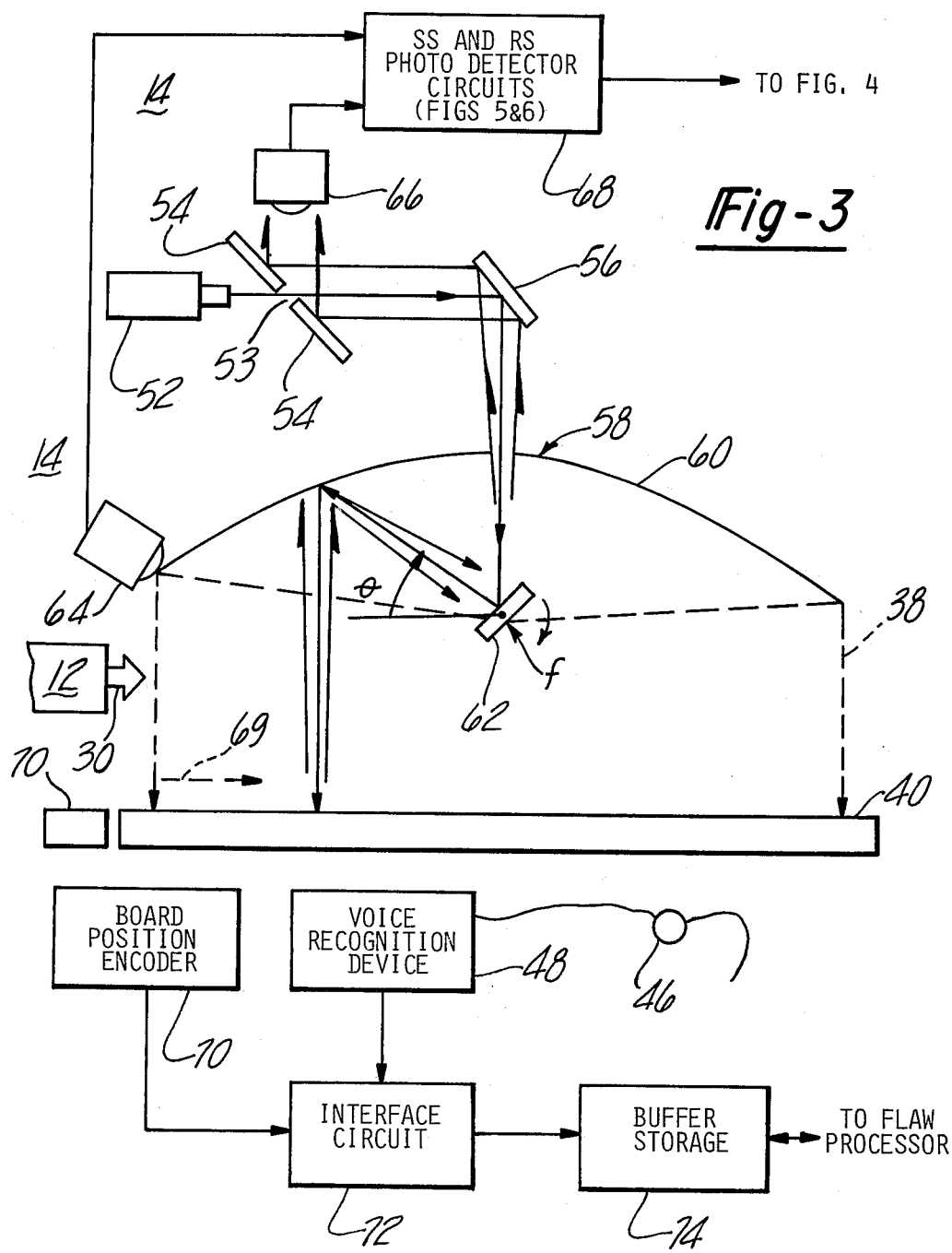
FIG. 3 is a schematic mechanical representation of the defect position scanner, including portions of associated circuitry in block diagram form.
Figure 4:
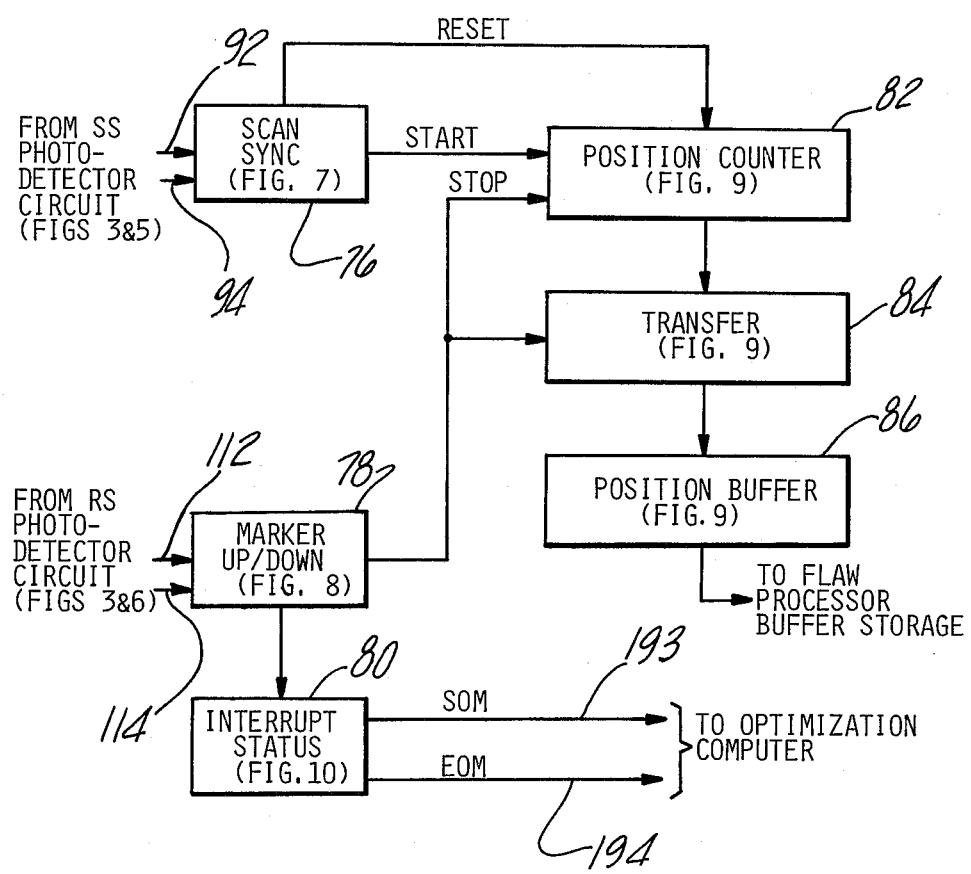
FIG. 4 is a functional block diagram of remote electrical circuitry associated with the defect position scanner.

Reference is made to FIGS. 3 and 4 which show mechanical schematics of the defect position scanner 14 and block diagrams of associate circuits. In the preferred embodiment, a beam of light is projected from a 3-4 milli-watt laser 52 through an aperture 53 of the planar mirror 54 onto a second fixed planar mirror 56. The beam is then reflected through aperture 58 which is centrally located when a 32 inch wide parabolic reflector 60 onto a rotating mirror 62. In the preferred embodiment, the mirror 62 contains two parallel reflecting surfaces and rotates clockwise at 60 revolutions per second about an axis through the focal point f of the parabolic reflector 60.

The laser beam reflected by the rotating mirror 62 will in turn be reflected by the parabolic reflector 60 onto the retro reflector 40 to generate a moving beam scan or light curtain 38 perpendicular to the direction of board motion. The moving beam will be generated at a rate of 120 scans per second in the direction indicated by the dotted arrow 69. The retro-reflected beams are returned (with some divergence, which is suggested by half arrows) along their respective incident beams to mirrors 56 and 54 and are detected by the retro-reflector signal photodetector 66.

One advantage of the present system is achieved by using the apertured mirror 54 as opposed to beam splitters employed in prior systems. Beam splitters by their very nature "split" the intensity of incident laser beam; this deficiency is eliminated by the present invention.

A start scan (SS) photodetector 64 is positioned adjacent one end of the parabolic reflector 60 (the left end, as shown, for clockwise rotation of the rotating mirror 62) and a retro-reflected signal (RS) photodetector 66 is positioned to detect light reflected by the fixed mirror 54 opposite the laser 52. The outputs from the SS and RS photodetectors 64 and 66 are transmitted to SS and RS photodetector circuits 68 via shielded cables to the digital position counter and associated circuitry (shown in FIG. 4) and located at an interface to the flaw processor 18. In particular, the RS photodetector 66 detects the interruption of the retro-reflected signal and transmits a signal to the marker up/down circuit 78 which in turn generates a signal to stop the count in the position counter 82 and to transfer the present count via transfer circuitry 84 into storage registers of the position buffer circuit 86 for later transfer to the data buffer storage of the flaw processor 18. The output signal of the marker up/down circuit 78 is also transmitted to the interrupt status circuit 80. The interrept status circuit 80 generates and transmits a start of mark ("SOM") signal to the optimization computer 20. The SOM signal informs computer 20 that defect information is stored in the position buffer circuit 86, and permits the computer 20 to process that defect information in accordance with the present position of the leading edge of the board and the defect position scanner zero reference point (starting position of scanner). The board leading edge information is generated by the board position encoder 70 which is located adjacent to the defect position scanner 14.

Information in the position buffer circuit 86 is not transferred to the computer 20 until another interrupt signal such as the end of mark (EOM) signal is received. When the marker 50 is removed from the light curtain 38 (indicating the end of a flaw), the RS photodetector 66 detects the removal (change in the light intensity) and energizes the marker up/down circuit 78 to stop the position counter 82 and to transfer the position information i.e., the present count in the position counter 82 to the position buffer circuit 86 and to energize the interrupt status circuit 80 to transmit an end of mark ("EOM") signal to the computer 20.

The electrical schematic wiring diagram for the start scan photodetector circuit 76 is shown in FIG. 5 and includes the start scan photodetector 64 (Type SGD100) having its output connected to a positive reference potential and to the positive input of comparator 88 such as Type LM111 through a coupling capacitor. The negative input of the comparator 88 is connected as shown to a negative reference potential through a noise filter. The output of the comparator 88 is connected to a low impedence Type DM 8830 driver circuit 90 having a differential output. Lines 92 and 94 are shielded cables which supply the differential output to the scan sync circuit 76 shown in FIG. 7.

The electrical schematic wiring diagram of the retro-reflected signal (RS) photodetector circuit is shown in FIG. 6. The retro-reflected signal photodetector 66 (Type SGD160) is connected to a negative potential. Its output terminals are connected to the negative and grounded positive input terminals of a Type SV536 comparator 96. The output of the comparator 96 is applied via a resistor 98 to the negative input of a Type 2530 amplifier 100. Output level adjustments are provided by resistors 102, the center tap of a potentiometer 104 and a resistor 106 which is connected to the positive input of the amplifier 100. The output of the amplifier 100 is applied to the input of a Type LM111 amplifier 108. The output of amplifier 108 is connected to a low impedance Type DM 8830 driver circuit 110 which has a differential output. This output signal is carried over shielded lines 112 and 114, to the marker up/down circuit 78 (FIG. 8).

Figure 7:
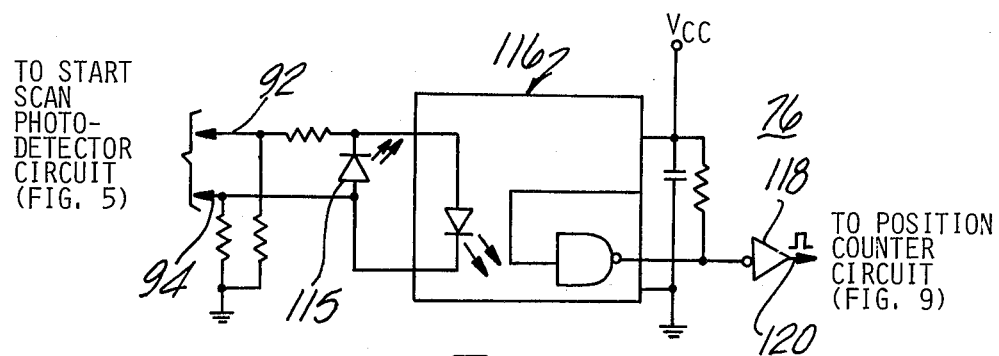
FIG. 7 is an electrical schematic wiring diagram of the scan sync circuit of FIG. 4.
Figure 8:
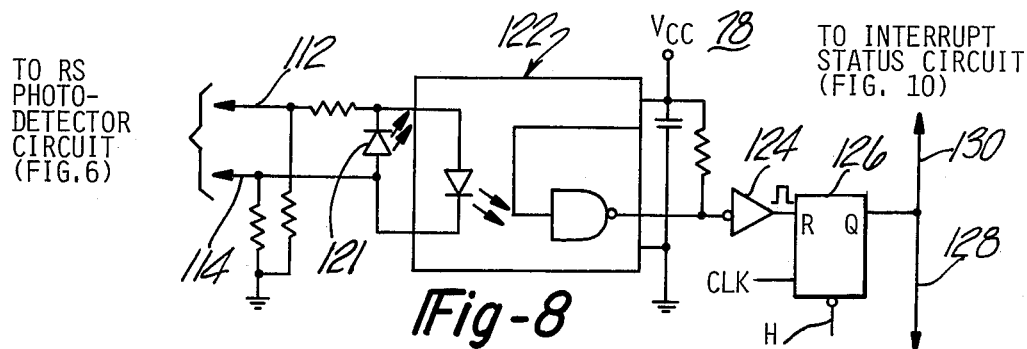
FIG. 8 is an electrical schematic wiring diagram of the marker up/down circuit of FIG. 4.

FIGS. 7 and 8 are electrical schematic wiring diagrams of the scan sync circuit 76 and marker up/down circuit 78, respectively. The input signals to the scan sync circuit 76 are received from differential output of the driver circuit 90 via lines 92 and 94. Lines 92 and 94 are connected to an opto-isolator such as Type 6N137. A light emitting diode 115 is connected across lines 92 and 94 in parallel with the opto-isolator 116. The light emitting diode 115 provides a balanced impedance matching termination of lines 92 and 94. The output from the optoisolator 116 is connected to a trigger circuit 118 which produces a short output pulse on a line 120 to reset and to start the position counter circuit 82 (FIG. 9). The trigger circuit 118 such as a Schmitt trigger will produce an output pulse in correspondence with each start of scan signal detected by photodetector 64.

Figure 10:
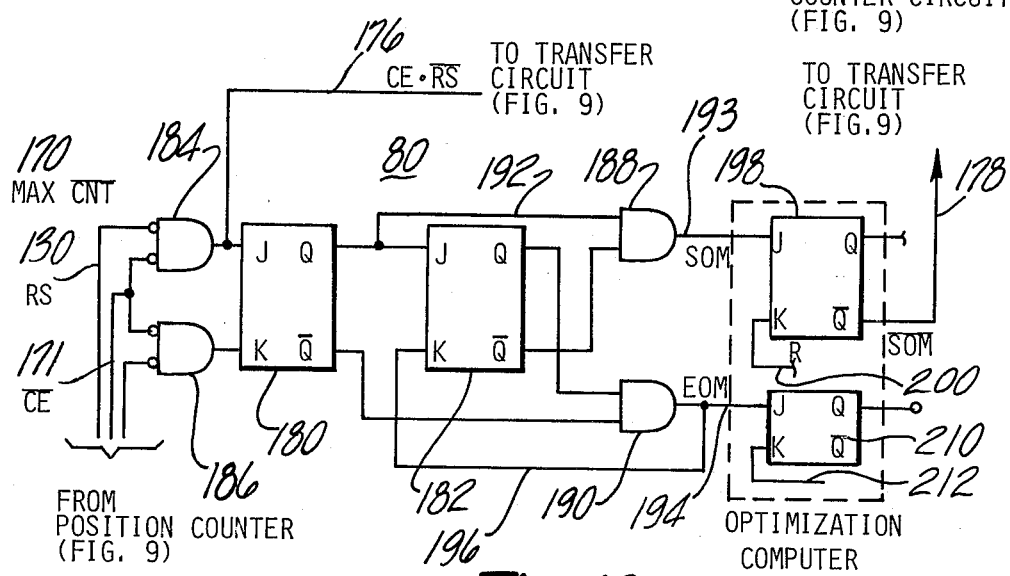
FIG. 10 is an electrical schematic wiring diagram of the interrupt status circuit of FIG. 4.

The marker up/down circuit 82 (FIG. 8) receives input signals from the driver circuit 110 of the retroreflected signal photodetector circuit via lines 112 and 114. The input lines 112 and 114 are connected to an optoisolator 122 having an impedance balancing light emitting diode 121 connected thereacross. The output of the opto-isolator 122 is connected to trigger circuit 124 which is connected to flip-flop 126. The output of flip flop 126 is transmitted via a line 128 to the position counter circuit 82 (FIG. 9) and via line 130 to the interrupt status circuit 80 (FIG. 10). The outputs from the marker up/down circuit 78 stop the position counter circuit 82 when the retro-reflected signal is interrupted by a marker 50 and permits the transfer of data representative of the position of the marker (indicating the beginning of a flaw) from the position counter circuit 82 to the position buffer circuit 86 for use by the flaw processor 18 and energizes the interrupt status circuit 80 to transmit a start of mark (SOM) signal to the flaw processor 18 to inform the flaw processor 18 that data is available in the position buffer circuit 86 for processing. In addition, when the marker 50 is removed from the light curtain 38, the outputs from the marker up/down circuit 78 again stop the position counter circuit 82 to permit the transfer of the end of flaw position data from the position counter circuit 82 to the position buffer circuit 86 and further energizes the interrupt status circuit 80 to transmit an end of mark (EOM) signal to the flaw processor 18 which subsequently processes the data in the position buffer circuit 86.

The electrical schematic of the position counter circuit 82, transfer circuit 84 and position buffer circuit 86 are shown in FIG. 9. The output from the scan sync circuit 78 (line 120) is connected to the J input of a position counter preconditioning flip flop 154. The output of marker up/down circuit 78 is connected via line 128 to the K input of the preconditioning flip flop 154, to the inverting input of an OR gate 156 and to AND gate 158. The output of AND gate 158 which is connected to the J input of a counter enable flip flop 160. The Q output of the preconditioning flip flop 154 is connected to the other input and the AND gate 158. The $\overline{Q}$ output of the preconditioning flip flop 154 is connected via a line 161 to one input of an AND gate 164 and connected via a line 166 to the inverted clearing or reset input of the 4 Bit counters 132, 134, and 136. The output of the OR gate 156 is connected to the second input of the AND gate 164; the output of which is connected to the K input of the counter enable flip flop 160. The $\overline{Q}$ output of the counter enable flip flop 160 (i.e., signal $\overline{CE}$) is transmitted via a line 171 to the interrupt status circuit 80 of FIG. 10.

The Q output of the counter enable flip flop 160 is connected via input line 138 to the counter 162. In the preferred embodiment, the counter 162 is a three stage counter having three 4-bit binary counters 132, 134 and 136. Input line 138 is connected in common to the enable or start terminal of each of the counters (130, 132 and 136). A counter reset signal for each of the counters is provided by connecting the $\overline{Q}$ output of the preconditioning flip flop 160 to the appropriate reset terminal of counters 132, 134, and 136. The eight most significant bits of the counter 162, namely the four outputs of counters 134 and 136 are connected to the input terminals of the bistable latches 144 and 146 respectively. The latches 144 and 146 form the buffer circuit 86. The output of latches 144 and 146 namely lines 148 and 150, respectively contain the position data to be transferred to the flaw processor under control of the transfer circuit 84.

One skilled in the art will appreciate that the counter 162 is not limited to a three stage counter and that other counters may be substituted to comport with the resolution of the defect position scanner 14. A maximum count (MAX CNT) NAND gate 152 is connected as shown to the output lines 140 and 142 of the counters 134 and 136, respectively, and is configured to produce a low output signal when a predetermined maximum count is reached by the position counter 162. This low output signal is generated immediately prior to the time that the laser beam reaches the end of its scan along the parabolic reflector 60. The output of the MAX CNT NAND Gate 152 is also connected via a line 168 to the second inverted input of the OR gate 156 and via a line 170 to the interrupt status circuit 80.

The transfer circuit 84 of FIG. 9 includes a NAND gate 172 having an output line 174 that is connected to the toggle input of each of the bistable latches 144 and 146. The inputs lines 176 and 178 to the NAND gate 172 transmit the output signals from the interrupt status circuit 80 and the optimization computer 20.

FIG. 10 shows the electrical schematic for the interrupt status circuit 80 and includes two flip flops, 180 and 182, and four AND gates 184, 186, 188 and 190. The output line 130 for the marker up/down circuit 78 is connected to one inverted input of the AND gate 184. The $\overline{Q}$ output of the counter enable flip flop 160 is transmitted from the position counter circuit 82 via the line 171 to the second inverted input of the AND gate 184 and to one inverted input of the AND gate 186. The output of the MAX CNT NAND gate 152 is connected via the line 170 to the second inverted input of the AND gate 186. The output of the AND gate 184 is connected to the J input of the flip flop 180 and to one input of the NAND gate 172 in the transfer circuit 84 via the line 176 (FIG. 9). The output of the AND gate 186 is connected to the K input of flip flop 180. The Q output of flip flop 180 is connected to the J input of the flip flop 182 and connected via line 192 to one input of the AND gate 188. The $\overline{Q}$ output of the flip flop 180 is connected to one input of the AND gate 190. The $\overline{Q}$ output of the flip flop 182 is connected to the second input of the AND gate 188, and the Q output of the flip flop 182 is connected to the second input of the AND gate 190. The outputs of the AND gates 188 and 190 represent the start of mark (SOM) and end of mark (EOM) signals respectively and are transmitted via lines 193 and 194 to an EOM flip flop 210 in the optimization computer 20. The output of the AND gate 190 is also transmitted via a line 196 to the K input of the flip flop 182. More particularly the SOM output signal is connected via line 193 to the J input of a flip flop 198 in the interface circuit of the flaw processor 18 in the optimization computer 20. The $\overline{Q}$ output of the flip flop 198 is transmitted via the line 178 to the other input of the NAND gate 172 in the transfer circuit 84 (FIG. 9). A reset signal (R) is generated internally in the optimization computer 20 on line 200 to reset the flip flop 198 following processing of the start of mark position information in the position buffer circuit 86.

The detailed operation of the defect position scanner will now be described with particular reference to FIGS. 5 through 12. As a board 10 is conveyed at a known and preferrably constant speed through the defect position scanner 14, the board position encoder 70 transmits signals (which are representative of the distance from the board's leading edge to a predetermined point in the inspection system 12) to the interface circuit 72 which combines the position signals, together with defect classification signals from the voice recognition device 48, into a computer-useable format. The resulting data is transmitted to the buffer storage 74 where it is available for processing by the flaw processor 18. The light curtain 38 is generated and the rotating laser beam causes a scan sync signal to be generated; the counter 163 is reset and the counter control namely flip flops 154 and 160 are armed. More particularly, the start scan photodetector 64 detects the laser beam at the beginning of each scan just before the laser beam reaches the parabolic mirror 60 and generates a pulse (Line 1, FIG. 11). This pulse causes the driver 90 (FIG. 5) to produce a differential output via lines 92 and 94 which energizes the opto-isolator 116 (FIG. 7) and the trigger 118 of the scan sync circuit 76. The trigger 118 transmits a short pulse output via line 120 to the position counter circuit circuit 82 which sets the counter preconditioning flip flop 154 (FIG. 9) and resets counters 132, 134 and 136 via the line 166.

After the laser beam passes the start scan photodetector 64 and enters the parabolic mirror 60 the retro-reflective (retro) signal is returned. The retro-signal (see FIG. 11, line 2 or FIG. 12, line 2) remains high as long as the beam is not interrupted by a marker or until the beam passes off the other end of the parabolic mirror 60. In the preferred embodiment the duration of each retro-signal is about 4 milliseconds, with two retro returns for each revolution of the scanning mirror 62 assuming a two-sided mirror (see FIG. 11).

The first presence of a retro-signal after a start scan signal enables the counter control (flip-flop 154 and 160) and starts the counter 162. As previously mentioned, this counter is a 3-stage 12 bit counter having a full count capacity of 4096, however, only the eight most significant bits are used for location information. In addition the preferred embodiment of the invention uses a 32 inch parabolic mirror 60 which in cooperation with the eight information bits provides a resolution of 32/256 or 0.125 inches.

The maximum count (output of AND gate 152) is set at a value that is less than the counter capacity (4096) and less than the count corresponding to the time when the retro-signal level drops as the incident beam goes off the end of the parabolic mirror 60. Under these uninterrupted conditions, no computer interrupts are generated and nothing is transferred to the position buffer.

As an example assume that the beam has not been interrupted, the retro-reflected signal detector 66 detects the reflected uninterrupted beam and causes the driver 110 (FIG. 6) to produce a differential output via lines 112 and 114. This energizes the opto-isolator 122 (FIG. 8) and trigger 124, thereby producing an output pulse which sets the flip-flop 126. The output from the flip-flop 126, transmitted via line 128, enables the AND gate 158 thereby setting the counter enable flip-flop 160 and starts the counters 132, 134 and 136. The signal transmitted via line 128 also permits the preconditioning flip-flop 154 to be reset when the next clock pulse is received. As mentioned previously the counters are set to reach a predetermined maximum count before the end of each scan. When the maximum count is reached, the output signal transmitted from the MAX CNT NAND gate 152 enables the OR gate 156 and the AND gate 164 and resets the counter enable flip-flop 160 following receipt of the next successive clock pulse.

The first time the retro-signal is interrupted before the occurrence of the maximum count by a marker 50, located at any position $P_1$ within the work area (line 1, FIG. 12), inserted in the bean curtain the following actions take place:

(a) The position counter 162 is stopped;
(b) The counter control (154, 160) is disabled;
(c) The count in counter 162 is transferred to the position buffer 86 (line 3, FIG. 12). Line 4, FIG. 12 illustrates the contents of the position buffer.
(d) A stark-of-mark (SOM) pulse is generated to set the SOM interrupt flip-flop 198 in the computer interface; and
(e) The pen indicator signal (marker up/down circuit 78) is activated to indicate that a marker 50 is present in the light curtain (line 9, FIG. 12).

On subsequent scans while the marker 50 is still in the curtain, the position counter 162 continues to count up to the present marker location ($P_2$, $P_3$, etc.) within the defect position scanner 14, however, no transfers are made to the position buffer 84. The first position value ($P_1$) remains in the buffer until it is read by the computer and a handshake pulse (see line 200, FIG. 10) resets the SOM flip-flop 198. After the SOM flip-flop 192 is reset, an updated position ($P_2$, $P_3$, etc.) is transferred into the buffer 86 on each scan, but no interrupts are generated. Thus, the position of marker 50 is continuously monitored permitting the operator to move the marker 50 from its initial position.

When the marker is withdrawn from the light beam curtain 38, there will be a first occurrence of a scan in which the maximum count is reached i.e., no beam interruption. During this first scan (which reaches maximum count before a retro-signal interruption) the following actions take place:

(a) The max count signal (output of AND gate 152) disables the counter control (flip-flop 160);

(b) An end-of-mark (EOM) pulse is generated to set the EOM flip-flop 210 in the computer interface;

(c) The last updated marker position remains in the position buffer (P$_7$). This data represents the location of the marker position with the light curtain 38 just before it was withdrawn; and (d) The pen indicator signal (marker up/down circuit 78) is deactivated showing that the marker has been removed.

The last marker position (P$_7$) remains in the position buffer 86 until read by the computer 20. A handshake signal (line 121) then resets the EOM flip-flop 210 in the computer interface. Subsequent scans now revert to the initial no-marker condition wherein the counter resumes counting up to the maximum count each time, but there are no transfers to the position buffer 86, and no computer interrupts.

A further more detailed description of the operation of the system can be seen from the following. Assuming that an indicator or marker 50 is inserted by the inspector into the light curtain 38, the retro-reflected signal is interrupted (see FIG. 11, line 2 and FIG. 12, line 2), the opto-isolator 122 (FIG. 8) becomes deenergized and the output of the flip-flop 126 becomes low. The low signal transmitted via line 128 disables the AND gate 158 and resets (following the next clock pulse) the counter enable flip-flop 160 (via the OR gate 156 and the AND gate 164), stopping the position counter circuit 82. The signals $\overline{CE}$ and RS are transmitted via lines 171 and 130, respectively, to the interrupt status circuit 80 where they are inverted and enable the AND gate 184, setting the flip-flop 180. The high Q output from the flip-flop 180 enables the AND gate 188 and a start of mark (SOM) signal is transmitted via the line 176 to one input of the NAND gate 172 (FIG. 9). The SOM signal informs the optimization computer 20 that flaw data corresponding to the position of the marker 50 in the light curtain 38, is contained in the position buffer circuit 86. Following receipt of the SOM signal, the optimization computer 20 generates a reset signal on line 200, the flip-flop is reset, and a high $\overline{SOM}$ signal is transmitted via the line 178 to the other input of the NAND gate 172 (in the transfer circuit 84). NAND gate 172 is enabled and sends an output signal via line 174 to the binary latches 148 and 150 permitting the data contained in the counters 134 and 136, to be transferred via lines 140 and 142, respectively, into the bistable latches 144 and 146. The data in the binary latches 144 and 146 is then transferred via lines 148 and 150, respectively, to the data bus of the flaw processor 18 under the control of the optimization computer 20.

Since the count in the counter circuit 82 was stopped when the retro-reflected signal was interrupted by the marker 50, the counter circuit 82 remains disabled for the remainder of the scan. As long as the marker 50 remains in the light curtain 38, a new count is initiated in the position counter circuit 82 during each subsequent scan. The position counter circuit 82 runs until the marker 50 (whether or not the marker 50 is in the same position in the light curtain 38) interrupts the retro-reflected signal, and the counter circuit 82 is stopped by the low output signal transmitted from the marker up/down circuit 78 via line 128, enabling the OR gate 156 and the AND gate 164, the output of which resets the counter enable flip-flop 160 following receipt of the next clock pulse. The data in the position counter circuit 82 is transferred to the position buffer circuit 86 following the interruption of the retro-reflected signal. However, no data is transferred from the position buffer circuit 86 in the absence of the transmission of another interrupt signal (i.e., an FOM signal) to the optimization computer 20. When the marker 50 is removed from the light curtain 38, the data corresponding to the position where the marker 50 last interrupted the retro-reflected signal is stored in the position buffer circuit 86 stopping the position counter circuit 82. The position counter circuit 82 will reach its maximum count near the end of the scan and the output of the MAX CNT NAND gate 152 goes low, enabling the OR gate 156 via line 168 and the AND gate 164 resetting the counter enable flip-flop 160 at the next clock pulse, causing its $\overline{Q}$ output ($\overline{CE}$) on the line 171 to one inverted input of the AND gate 186 (FIG. 10) to go high. The low output of the MAX CNT NAND gate 152 is also transmitted via the line 170 to the other inverted input of the AND gate 186 which is enabled and resets the flip-flop 180 at the next clock pulse. The AND gate 190 is enabled, and a high end of mark (EOM) interrupt signal is transmitted via line 194 to flip flop 210 in the interface of the optimization computer 20 which then transmits the data on the output lines 148 and 150 to the flaw processor 18. The EOM signal is also transmitted via the line 196 and resets the flip-flop 182 at the next clock pulse, disabling the AND gate 190, removing the high EOM signal and causing the Q input from the flip-flop 182 to go high, preparing the AND gate 188 to become enabled when a high signal is again present on the line 192.

Thus, it will be appreciated that an automated defect position scanner constructed in accordance with the invention provides a simple and accurate indication of the beginning and end positions of defects on the surface of a board passing through an inspector station without sacrificing inspection speed and without requiring physical attachments to the marker 50. The defect positions are referenced with respect to the beginning of individual scans and to the position of the front edge of the moving board as provided by the board position encoder 70 to the flaw processor 18. An inspector need not be concerned with providing information regarding defect sizes and classes at the instant the defect pass a fixed reference point, such as a hairline, but rather is provided with a "working field", approximately 2½ feet wide, within which information regarding one or more defects may be vocally input into the lumber inspection and optimization system 10. This permits the system to process information regarding a plurality of defects (including closely spaced and overlapping defects) at the desired inspection speed. Although the laser scan speed may be varied considerably, 120 scans per second has been found to be satisfactory. It has been found that the defect position scanner has a sensitivity which detects an approximate 1/16 inch diameter object when the position counter circuit 82 counts at a rate of approximately 4,000 counts for a 32 inch wide scan.

The point at which the beam was interrupted is measured along the scan direction as a function of time from the instant the retro-signal is detected after the start of scan. The rotating mirror is driven by a constant speed motor, providing a suitable time base. Due to the variable distance as the beam scans across from the rotating mirror to the parabolic surface, the movement of the beam in the scan direction across the inspection area is a nonlinear function of time (or rotating mirror angle.) Correction for this nonlinearity is accomplished by using a segment approximation (8 elements) to the distance/time curve. The correction table is stored in the memory of the optimization computer 20.

The two-sided rotating mirror 62 introduces some variation in the reflection point for the beam scan referenced to the parabola focal point. This causes some non-parallelism or skewing of the rays of the light curtain, with an associated position error. However, with a reasonably small mirror offset from the center of rotation this error is within the required accuracy of $\pm \frac{1}{4}$ inch.

It is intended that the preferred embodiment of the invention as described would be practice in combination with the electro-optic scanner 16 such as a scanning system disclosed by Idelsohn, et al in U.S. Pat. No. 4,149,089. In this mode of operation the flow information from the defect position scanner supplements the high accuracy flaw data derived from the electro-optical scanner 16. Because of the inherent accuracy of the defect position scanner i.e., a simpler though somewhat less accurate mode of operation can be achieved by eliminating the electro-optical 16 and using the defect positioning scanner 14 flaw data as the primary flaw data input to the optimization computer 20.

While the invention has been described with references to a particular embodiment thereof, it will be appreciated that various modifications in form and detail may be made therein without departing from the spirit and scope of appended claims.

Having thus described the invention, what is claimed is:

1. A system for detecting the positions of defects on at least one surface of a board of lumber comprising:
   conveyor means for moving the board in a predetermined direction at a predetermined speed;
   defect scanning means disposed along the conveyor means for generating a light curtain, having a moving light scan scanning at a predetermined frequency in a direction parallel to the predetermined direction and disposed slightly above and generally parallel to one surface of the board;
   encoder means for measuring the distance of the leading edge of the board past a predetermined point within the light curtain and for generating board leading edge position signals representative thereof;
   detector means, responsive to the interruption of the light curtain by an indicator indicating the leading edge of a particular defect on the moving board, for generating a position signal representative of the position of the leading edge of the defect within the light curtain and responsive to the removal of the indicator from the light curtain indicating the trailing edge of the defect on the moving board for generating position signals representative of the position of the trailing edge of the defect within the light curtain and;
   defect storage means for combining the board leading edge position signal, the defect leading edge and trailing edge position signals to generate defect position information in a defect data buffer containing signals representative of the positions of the leading edge and trailing edge of each particular defect on the board in usable coordinates.

2. The system of claim 1 further comprising:
   voice recognition means for converting voice defect class information into electrical defect class signals representative of the class of said particular defect in the light curtain; and
   means for combining the defect class signals with the data in said defect storage means corresponding to said particular defect.

3. A system for locating the position of particular defects disposed on a surface of a material, the system comprising:
   defect scanning means for generating a light curtain at a predetermined frequency, said light curtain having an incident moving light beam and a reflected light beam projected across a dimension of a region and scanning through said region in one direction which is generally perpendicular to said dimension;
   conveyor means for moving the material through said region in a direction generally perpendicular to said dimension and where said conveyor means maintains said material proximate to and below said moving light beam;
   detector means responsive to the interruption of said moving light beam during any particular scan for generating a first signal determination of the location of said interruption of said moving light beam within said region and for generating a second signal indicative of the location of the removal of the interruption within said region and where said first signal is determinative of the position of the leading edge a particular defect on said moving material within said region and where said second signal is determinative of the position of the trailing edge of said particular defect within said region.

4. The system as recited in claim 3 further including storage means for storing said first and said second signals.

5. The system as recited in claim 3 wherein said detector means further comprises:
   scan means responsive to said moving light beam for generating a scan sync signal prior to each scan of said moving light beam through said region;
   indicator circuit means responsive to said reflective signal for generating an indicator signal indicative of the interruption of said moving light beam;
   counter means having a maximum preset count responsive to said scan sync signal and said indicator signal for generating an output signal having a count proportional to the position of the location of the interruption within said region upon the occurrence of said indicator signal and for generating a signal corresponding to the maximum preset count during an uninterrupted scan of said incident light beam.

6. The system as recited in claim 5 wherein said detector means further comprises:
   first means for first resetting said counter means in response to each successive said scan sync signal;
   second means for starting said counter in response to each of said scan sync signal; and
   a third means for stopping said counter in response to said indicator signal.

7. The system as recited in claim 6 further including position buffer storage means for storing the count within said counter means upon the first occurrence of said indicator signal and for transferring said stored count to a remote device and for storing a subsequent count within said counter means during each successive scan cycle occuring thereafter and for transferring the last stored count within said counter means to said remote device upon the last occurrence about of said indicator signal.

8. The system as recited in claim 3 wherein said defect scanning means comprises:
   a parabolic reflector having a reflective surface thereon and having an aperture located at the midpoint of said parabolic reflector;
   retro-reflector means disposed apart from and opposite to said reflective surface;
   a multi-sided rotating mirror proximate to and rotable the focal point of said parabolic reflector;
   a first mirror located apart from said parabolic reflector oppositely situated from said rotating mirror;
   a source of radiation producing an incident light beam focused upon said first mirror and reflected by said first mirror through the aperture of said parabolic reflector; onto said rotating mirror; and
   a second mirror having a second aperture therein, said second mirror disposed between said source of radiation and said first mirror and oriented relative to said incident beam so that said incident beam is directed through the second aperture and where said above recited components cooperate so that said incident light beam is directed through said second aperture onto said first mirror wherein said incident light beam is reflected through said first aperture onto a surface of said multi-sided mirror, said multi-sided mirror causing said incident beam to impinge upon various portions of said reflecting surface of said parabolic reflector as determined by the degree of rotation of said rotating mirror and then upon said retro-reflector, said retro-reflector thereupon reflecting said incident beam back to said parabolic reflector then to said multi-sided mirror through said first aperture onto said first mirror and then onto said second mirror.

9. A scanning system for detecting the positions of defects disposed on a surface of a material which has a known location with respect to the apparatus, the aparatus comprising:
   defect scanning means for generating a light scan at a predetermined frequency in one direction across a region adjacent the surface of the material;
   detector means responsive during one scan to an interruption, designating a starting position of a defect, of the light in the region for generating a first signal indicative of the position in said one direction of the interruption in the region and responsive during a subsequent scan to a removal, designating an end position of the defect, of the interruption from the region for generating a second signal indicative of the position in said one direction of the removal of the interruption from the region.

10. The system of claim 9 further comprising:
   storage means for receiving and storing one of said first and said second signals, said detector means enabling said first signal to be stored herein before the detector means detects the removal of the interruption from the region and generates the second signal.

11. The system of claim 10 further comprising:
   first storage status means controlled by said detector means for enabling the transmission of said first signal from said storage means to a remote device before said second signal is generated.

12. The system of claim 11 further comprising:
   inhibiting means controlled by the remote device for preventing said second signal from being received by said storage means before said first signal is transmitted from said storage means to the remote device.

13. The system of claim 12 further comprising:
   second storage status means controlled by said detector means and said first storage status means for enabling the transmission of said second signal from said storage means to a remote device only after the transmission of said first signal from said storage means.

14. The system of claim 9 wherein the position detection means comprises:
   a first light detection circuit for generating a start sync output signal at the start of each scan;
   a second light detection circuit for detecting the light scanned across the region and for generating a first output signal when the light scan is uninterrupted and a second output signal when the light scan is interrupted and;
   a counter circuit means connected to said first and second light detection circuits, for maintaining up to a preset maximum count comprising signals representative of the instantaneous position of the light in the region during each scan, said counter circuit means being first reset and then started by the start sync output signal from the first light detection circuit at the start of each scan and stopped by said second output signal from the second light detection circuit when the light in the region is interrupted during a scan, said counter circuit means thereby being reset and started at the beginning of each successive scan and during succeeding scans until the interruption is removed and the counter circuit means reaches the preset maximum count.

15. A position detection system comprising:
   a source of radiation;
   a scanner for successively scanning the radiation across a predetermined region;
   a detector circuit for detecting the radiation as the radiation is scanned across the region and responsive to the absence of interruption of the radiation as the radiation is scanned to generate a first output signal and to an interruption in the radiation in the scan to generate a second output signal, ($\overline{RS}$); and
   circuit means coupled to said detector circuit and to said scanner for monitoring the instantaneous position of the radiation in the region as the radiation is scanned and thereacross, said circuit means responsive to said second output signal transmitted during one scan for transmitting electrical signals representative of the position of the interruption in the region during said one scan and to the first occurrence of the presence of said first output signal transmitted from said detector circuit during an entire subsequent scan for transmitting electrical signals representative of the position of the interruption in the region during the last preceding scan.

16. The position detection system of claim 15 wherein said circuit means comprises:
   a counter circuit means connected to said detector circuit and arranged to be reset by said detector circuit at the start of each scan, and to be stopped by said second output signal from said detector circuit when there is an interruption in the radiation during a scan, for maintaining, until stopped, a count which is representative of the instantaneous position of the radiation in the region during each scan;

a storage circuit for receiving and storing the count from said counter circuit means when the storage circuit has been enabled; and a transfer circuit connected to the detector circuit and between the counter circuit means and said storage circuit and responsive to receipt to said second output signal from said detector circuit for enabling the storage circuit.

17. The position detection system of claim 16 wherein the counter circuit means is arranged to transmit a first signal ($\overline{CE}$) when the counter circuit means has been running and has not been reset and a second signal ($\overline{MAX\ CNT}$) immediately prior to an end of a scan without an interruption of the detected radiation, where said counter circuit means has reached a preset maximum count and further comprising;

a status indication circuit, connected to the detector circuit and said counter circuit means for transmitting to a remote device first and second status signals indicating that a count to be transferred to the remote device is stored in said storage circuit, the status indication circuit further including transmitting means for sending:

the first status signal upon concurrent receipt of said $\overline{RS}$ and $\overline{CE}$ signals from said detector circuit and said counter circuit, respectively; and the second status signal, only after transmittal of the first status signal, upon concurrent receipt of the $\overline{CE}$ signal and the $\overline{MAX\ CNT}$ signal from said counter circuit.

18. A defect position scanning apparatus comprising:

a parabolic reflector having a reflective surface thereon and having an aperture located at the midpoint of said parabolic reflector;

retro-reflector means disposed apart from and opposite to said reflective surface;

a multi-sided rotating mirror proximate to and rotable about the focal point of said parabolic reflector;

a first mirror located apart from said parabolic reflector oppositely situated from said rotating mirror;

a source of radiation producing an incident light beam focused upon said first mirror and reflected by said first mirror through the aperture of said parabolic reflector onto said rotating mirror; and a second mirror having a second aperture therein, said second mirror disposed between said source of radiation and said first mirror and oriented relative to said incident beam so that said incident beam is directed through the second aperture and where said above recited components cooperate so that said incident light beam is directed through said second aperture onto said first mirror wherein said incident light beam is reflected through said first aperture onto a surface of said multi-sided mirror, said multi-sided mirror causing said incident beam to impinge upon various portions of said reflecting surface of said parabolic reflector as determined by the degree of rotation of said rotating mirror and then upon said retro-reflector, and retro-reflector thereupon reflecting said incident beam back to said parabolic reflector then to said multi-sided mirror through said first aperture onto said first mirror and then onto said second mirror.

19. A method of locating defects on the surface of a material, the steps comprising:

19.1 moving the material in a predetermined direction at a predetermined speed below a moving light curtain;

19.2 generating a light curtain of a determinable length comprising a moving light beam scanning between said determinable length at a predetermined frequency;

19.3 interrupting said moving light beam by inserting an indicator at a location within said light curtain corresponding to the leading edge of a particular defect on said moving board;

19.4 generating a defect leading edge signal or start of mark signal for each defect in response to the first interruption of said moving light beam in accordance with step 19.3;

19.5 permitting said moving light beam to return to its uninterrupted state by removing the indicator from said light curtain at a location within the light curtain corresponding to the location of the trailing edge of the particular defect on the moving board;

19.6 generating a defect trailing edge or end of mark signal in response to the return of the moving light beam to its interrupted state;

19.7 generating a signal indicative of the position of the leading edge of the board relative to a determinable location along said predetermined direction.

20. The method as recited in claim 19 including the following step:

combining said leading edge signal with said defect leading edge signal and said defect trailing edge signal to obtain defect coordinate data relative to the leading edge of the board.

21. A method of locating defects on the surface of a material and of enhancing the defects so located by introducing defect class of quality, the steps comprising:

21.1 moving the material in a predetermined direction at a predetermined speed below a moving light curtain;

21.2 generating a light curtain of a determinable length comprising a moving light beam scanning between said determinable length at a predetermined frequency;

21.3 interrupting said moving light beam by inserting an indicator at a location within said light curtain corresponding to the leading edge of a particular defect on said moving board;

21.4 generating a defect leading edge signal or start of mark signal for each defect in response to the first interruption of said moving light beam in accordance with step 21.3;

21.5 permitting said moving light beam to return to its uninterrupted state by removing the indicator from said light curtain at a location with the light curtain corresponding to the location of the trailing edge of the particular defect on the moving board;

21.6 generating a defect trailing edge or end of mark signal in response to the return of the moving light beam to its uninterrupted state;

21.7 generating a signal indicative of the position of the leading edge of the board relative to a determinable location along said predetermined direction.

21.8 combining said leading edge signal with said defect leading edge signal and said defect trailing edge signal to obtain defect coordinate data relative to the leading edge of the board;

21.9 generating vocal defect classification data in a relatively contiguous time frame with the generation of said defect leading edge signal;

21.10 combining said vocal defect classification data with said data as generated in Step 21.8.

22. The method as recited in claim 21 including the steps of:

suppressing certain defect data in correspondence with a determinable set of vocal defect classification data.

* * * * *